United States Patent [19]

Dewar

[11] Plant 4,383

[45] Feb. 20, 1979

[54] MUTATION OF SUMMERLAND RED McINTOSH APPLE TREE

[75] Inventor: Mac F. Dewar, Oyama, Canada

[73] Assignee: Stark Brothers Nurseries & Orchards Company, Louisiana, Mo.

[21] Appl. No.: 890,868

[22] Filed: Mar. 24, 1978

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

The new variety is a whole tree bud mutation of the Summerland Red McIntosh apple tree (non-patented) which was discovered in my orchard at Oyama, British Columbia, Canada. This variety is of the spur-type, possesses a vigorous compact more upright growth habit, and heavily bears fruit on a consistent basis which is of a more intense solid red color. It possesses more fruiting spurs per linear foot than the McIntosh apple tree — Gatzke strain (non-patented) and less fruiting spurs per linear foot than the McIntosh apple tree — Greenslade strain (U.S. Plant Pat. No. 2,982) and the McIntosh apple tree — Raikes strain (U.S. Plant Pat. No. 3,390). Additionally, its propensity to form shoots (i.e. vegetative growth) is different (as described) than that of the McIntosh apple tree — Gatzke strain, the McIntosh apple tree — Greenslade strain and the McIntosh apple tree — Raikes strain.

2 Drawing Figures

SUMMARY OF THE INVENTION

The new variety which is a whole tree bud mutation of the Summerland Red McIntosh apple tree was discovered by me in 1968 in my cultivated orchard (Lot E, Map 975) at Oyama, British Columbia, Canada. I was attracted to the new variety by the distinctive intense red color of its fruit and by its distinctive growing habit whereby heavy quantities of fruiting spurs are borne on two and three year old wood. The fruit of the new variety, accordingly, is borne on shorter and heavier fruiting spurs which are more closely spaced and in greater numbers than found on the Summerland Red McIntosh apple tree and other standard bearing McIntosh apple varieties. Fruit production begins at an earlier age if good horticultural practices are followed. The new variety, because of its only slightly spreading tendency, has the ability to better sustain heavy crops of fruit without breakage. The characteristics of the new variety are also different than those of other spur-type McIntosh apple varieties.

The new variety of apple tree possesses the following combination of characteristics:

(a) a vigorous compact more upright growth habit with only a slightly spreading tendency, (b) the ability to heavily bear fruit which is of a more intense red color, (c) large dark green leaves, (d) more fruiting spurs per linear foot than the McIntosh apple tree — Gatzke strain (non-patented), (e) less fruiting spurs per linear foot than the McIntosh apple tree — Greenslade strain (U.S. Plant Pat. No. 2,982) and the McIntosh apple tree — Raikes strain (U.S. Plant Pat. No. 3,390), (f) the propensity to form when three years of age significantly less shoots on two year old branches than the McIntosh apple tree — Gatzke strain (non-patented) and the McIntosh apple tree — Greenslade strain (U.S. Plant Pat. No. 2,982), (g) the propensity to form when three years of age more shoots on two year old branches than the McIntosh apple tree — Raikes strain (U.S. Plant Pat. No. 3,390), and (h) the propensity to form after three years of age generally less shoots than the McIntosh apple tree — Gatzke strain (non-patented).

The Gatzke strain McIntosh apple tree referred to above is marketed by the Stark Bro's Nurseries and Orchards Company under the registered trademark "Starkspur".

Asexual propagation beginning in 1970 has demonstrated that the unique combination of characteristics of this new variety comes true to form and is established and transmitted through succeeding propagations.

DETAILED DESCRIPTION OF THE DISCLOSURE

Figure 1:
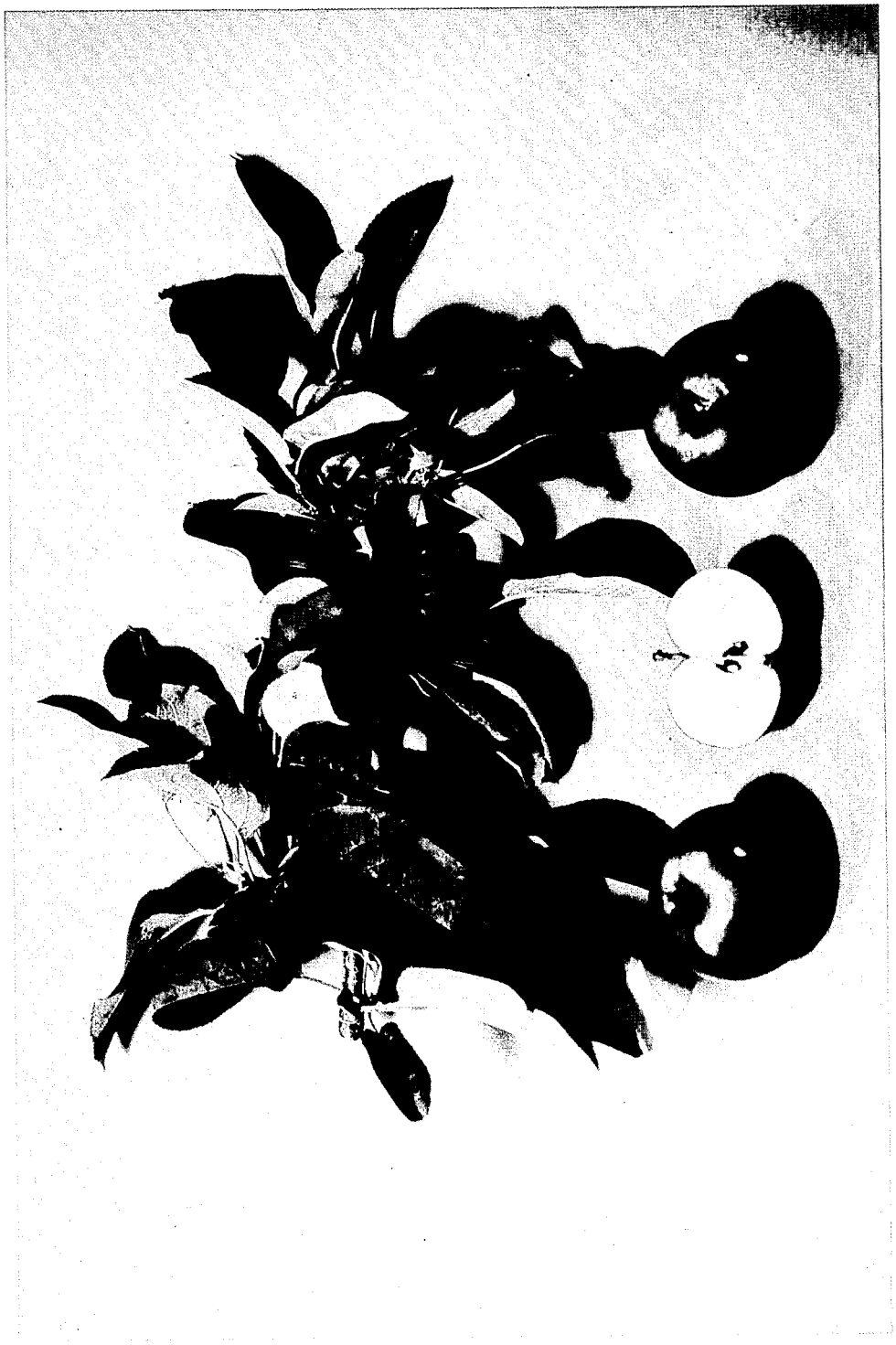
FIG. 1 shows in color as true as is reasonably possible typical specimens of the foliage and fruit of the new variety of apple tree.
Figure 2:
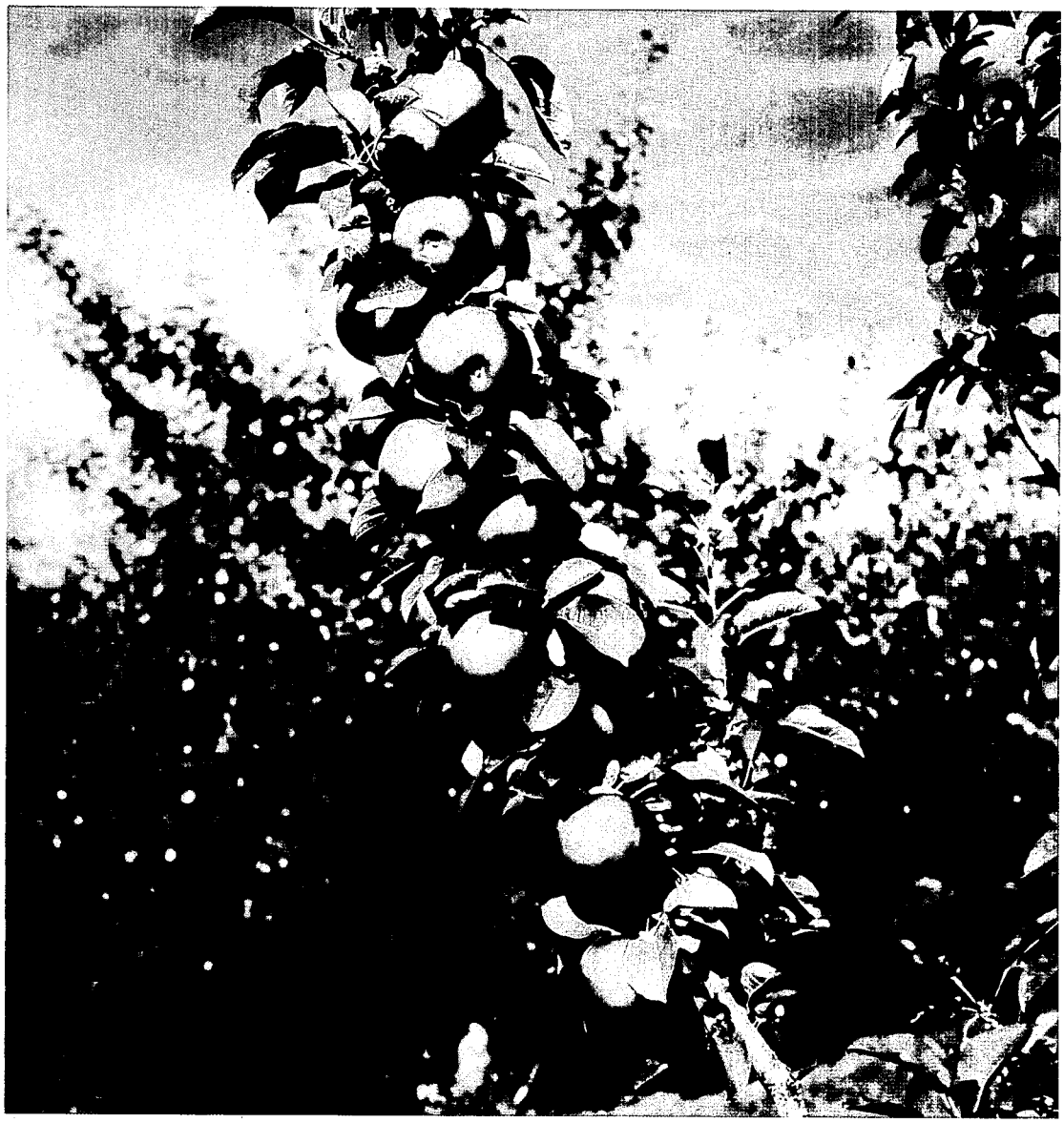
FIG. 2 shows in color as true as is reasonably possible a typical substantially upright fruit-bearing limb of the new variety of apple tree.

The following is a detailed description of my new variety with color terminology in accordance with the Nickerson Color Fan except where general color terms of ordinary dictionary color significance are obvious.

The specimens described were grown at Oyama, British Columbia, Canada.

The dates of first and last pickings are the same as those of the Summerland Red McIntosh apple tree (non-patented), and commonly are about September 15, and September 30, depending upon specific growing conditions encountered.

Tree: Medium; vigorous; upright — slightly spreading, tall; vase-formed; rapid growing; hardy; very productive; regular bearing.

*Trunk.*—Stocky; smooth.

*Branches.*—Thick; smooth, much branching; grey.

*Lenticels.*—Medium.

*Leaves.*—Length — about 3½ inches; width — about 2-7/16 inches; medium long; medium wide; ovate; abruptly pointed; thick; Dark Green — Hue 2.5G 3/3; rugose.

*Margin.*—Coarsely serrate.

*Petiole.*—Length — about 1¼ inches; medium long; medium thick.

Flowers: Dates of first and full bloom are the same as the Summerland Red McIntosh apple tree; early; large; white.

Fruit: Firm apple — September 21.

*Size.*—Uniform — some may be variable; axial diameter — about 2-9/16 inches; transverse diameter — about 3 inches; oblate.

*Cavity.*—Symmetrical; flaring toward apex; acuminate; even; undulate; depth — about ½ inch; breadth — about 1¼ inch; markings, none.

*Basin.*—Symmetrical; rounded; pubescent; depth — about ½ inch; breadth — about 1½ inches; markings, none.

*Stem.*—Medium to stout; pubescent; length — about ½ inch; breadth — about 1/16 inch; markings — 1 or 2 bracts present.

*Calyx.*—Closed. Segments — persistent; narrowly lanceolate; acute; length — about 3/16 inch; separated; ascending; converged from base toward center. Outer surface — pubescent. Inner surface — pubescent.

*Eye.*—Small to non-existent; partially closed.

*Skin.*—Thin; tough; glossy; waxed. Dots — obscure; many; even; submerged; circular; aerolar. Color of dots — very light green.

Distribution of dots — fairly even. Ground color — greenish white to yellow. Color markings — blushed; bright; some fruit faintly striped like Summerland Red McIntosh apple tree. Color of markings — blushed. Bloom — moderate. Scarfskin — wanting. General color effect — between Strong Red and Dark Red — Hue 2.5R 4/10 to 2.5R 3/7. Color intensity better than Summerland Red McIntosh apple tree but similar to McIntosh apple tree — Greenslade strain (U.S. Plant Pat. No. 2,982 and McIntosh apple tree — Raikes strain (U.S. Plant Pat. No. 3,390).

*Flesh.*—Rather juicy. Color of flesh — white with yellowish-greenish tint. Texture — tender; fine. Flavor — sweet, sprightly. Aroma — distinct. Quality — best.

*Core.*—Median. Bundle area (longitudinal section) — medium; broadly ovate; unsymmetrical at base; opposite; with cell. Halves of area — unequal; inconspicuous; in one whorl.

Alternate bundle — approximate to distant — reaches tube at stamens. Core lines — meeting; in cross section indistinct; carpellary area distinct. Calyx-tube — glabrous toward base; apex broadly obconic; funnel form. Stem of funnel — short. Depth of tube to shoulder — about ¼ inch. Entire depth — about ½ inch. Styles — present; united. Stamens — two obscure; whorls; median. Auxillary cavity — wanting. Seed cells axile — open. Cell walls — distant; thick; tough. Length — about ¾ inch. Breadth — about 7/16 inch. Longitudinal section — broadly oval; obtuse at apex. Surface — entire; smooth. Cross section — broad.

*Seeds.*—Number perfect 5–8; imperfect 0–3. Number in one cell — maximum 3. Length — about ¼ inch. Breadth — about 3/16 inch. Form — acute. Color — brown; light to dark.

Use: Multiple use.

Keeping quality: Good.

*Number of days in ordinary storage.*—Same as all true McIntosh.

Resistance to:

*Insects.*—Medium.

*Diseases.*—Medium.

I claim:

1. A new and distinct variety of apple tree of the spur-type which is a whole tree mutation of the Summerland Red McIntosh apple tree (non-patented) substantially as shown and described, characterized by a vigorous compact more upright growth habit with only a slightly spreading tendency, the ability to heavily bear fruit which is of a more intense red color, large dark green leaves, more fruiting spurs per linear foot than the McIntosh apple tree — Gatzke strain (non-patented), less fruiting spurs per linear foot than the McIntosh apple tree — Greenslade strain (U.S. Plant Pat. No. 2,982) and the McIntosh apple tree — Raikes strain (U.S. Plant Pat. No. 3,390), the propensity to form when three years of age significantly less shoots on two year old branches than the McIntosh apple tree — Gatzke strain (non-patented) and the McIntosh apple tree — Greenslade strain (U.S. Plant Pat. No. 2,982), the propensity to form when three years of age more shoots on two year old branches than the McIntosh apple tree — Raikes strain (U.S. Plant Pat. No. 3,390), and the propensity to form after three years of age generally less shoots than the McIntosh apple tree — Gatzke strain (non-patented).

* * * * *